United States Patent [19]
Yano et al.

[11] Patent Number: 5,624,687
[45] Date of Patent: Apr. 29, 1997

[54] QUICK-DISSOLUTION SOLID PREPARATION

[75] Inventors: Katsuhiko Yano, Fujieda; Yasuhiro Nishizono, Urawa; Shigeru Yamazaki, Fujieda; Tadayoshi Ohmura, Fujieda; Shunji Hasumi, Fujieda, all of Japan

[73] Assignee: Yamanouchi Pharmaceutical Co., Ltd., Tokyo, Japan

[21] Appl. No.: 137,054

[22] PCT Filed: Apr. 14, 1992

[86] PCT No.: PCT/JP92/00469

§ 371 Date: Oct. 15, 1993

§ 102(e) Date: Oct. 15, 1993

[87] PCT Pub. No.: WO92/18109

PCT Pub. Date: Oct. 29, 1992

[30] Foreign Application Priority Data

Apr. 15, 1991 [JP] Japan ................. 3-109896

[51] Int. Cl.⁶ ........................................ A61K 9/14
[52] U.S. Cl. ....................... 424/490; 424/494; 424/497
[58] Field of Search ......................... 424/490, 494, 424/464, 497

[56] References Cited

U.S. PATENT DOCUMENTS

| | | | |
|---|---|---|---|
| 4,101,651 | 7/1978 | Kobayashi et al. | 424/489 |
| 4,673,564 | 6/1987 | Kawata et al. | 424/494 |
| 5,026,560 | 6/1991 | Makino et al. | 424/494 |
| 5,213,811 | 5/1993 | Frisbee et al. | 424/494 |
| 5,223,268 | 6/1993 | Stetsko et al. | 424/494 |
| 5,300,304 | 4/1994 | Sheth et al. | 424/494 |

FOREIGN PATENT DOCUMENTS 116414  7/1983  Japan.

*Primary Examiner*—Amy Hulina
*Attorney, Agent, or Firm*—Burgess, Ryan and Wayne

[57] ABSTRACT

The invention provides a solid preparation having a quick and pH-independent dissolution with an excellent bioavailability for a drug that is otherwise sharply depressed in solubility with pH elevation. This solid preparation contains granules each comprising a fine particulate core coated with a solid solution comprising a drug which is pH-dependent in solubility and may be released from an enteric base-containing composition at low pH and an enteric base.

4 Claims, 5 Drawing Sheets

QUICK-DISSOLUTION SOLID PREPARATION

TECHNICAL FIELD

This invention relates to a pH-independent quick-dissolution solid preparation containing as a principal agent a drug which is otherwise rapidly depressed in solubility with pH elevation.

BACKGROUND ART

A quick-dissolution solid preparation is designed to achieve a rapid rise in the blood concentration of a drug administered orally in expectation of the immediate action of the drug. Therefore, in designing a quick-dissolution solid preparation, the disintegration of pharmaceutical per se, solubility and bioavailability of the drug are important considerations.

However, a drug which is sharply depressed in solubility with pH elevation is generally less efficiently absorbed in the stomach than in the intestinal tract even if it is highly disintegrable and is soluble in the gastric juice and, therefore, has the disadvantage of low bioavailability. Another disadvantage of such a drug is that it can hardly exhibit its expected efficacy in patients with achlorhydria or gastric hypoacidity.

For the purpose of enhancing the solubility of a hardly soluble drug, it is known to disperse the drug in substantially amorphous state in an inert carrier such as polyvinylpyrrolidone to thereby provide a solid solution (also known as solid dispersion) [cf. Chiou. W. L., Riegelman, S: *J. Pharm. Sci.,* 60, 1281 (1971) and JP-A-54-2316 (the term "JP-A" as used herein means an unexamined published Japanese patent application)].

It is also known, for improving the absorption of nifedipine which is a hardly soluble drug, to coat fine beads of a water-soluble pharmaceutical additive substance with a solid solution consisting of nifedipine and polyvinylpyrrolidone (JP-A-57-85316).

It is also disclosed in JP-A-56-110612 that a preparation prepared by mixing a hardly soluble drug with a base, such as polyvinylpyrrolidone, with or without addition of a surfactant or the like, granulating the resulting composition by the fluidized-bed granulating method, and compression-molding the resulting granules is excellent in disintegration, rate of absorption, and rapidity of dissolution. In this process, anhydrous calcium hydrogenphosphate, among others, is used as the core material for fluidized-bed granulation.

However, *Yakugaku Zasshi* 104(5), 485–489 (1984) reports that when the hardly soluble drug nifedipine is made into a solid solution using an enteric coating base such as hydroxypropylcellulose phthalate or methacrylic acid-methyl methacrylate copolymer and coating is carried out, the rate of dissolution in JP (Japanese Pharmacopoeia) Test Solution 1 is suppressed and it is, therefore, generally acknowledged that as long as an enteric base is employed, coating with a solid solution of a hardly soluble drug may not easily provide a quick-dissolution solid preparation.

DISCLOSURE OF INVENTION

In the above state of the art, the inventors of the present invention conducted extensive studies to develop a pH-independent quick-dissolution solid preparation for N-(1-benzyl-2-methylpyrrolidin-3-yl)-5-chloro-2-methoxy-4-methylaminobenzamide, inclusive of its salt, which is depressed in solubility with pH elevation, and found surprisingly that a solid preparation prepared from granules prepared by coating fine particulate cores with a solid solution consisting of the same compound and a definite amount of an enteric base is excellent in dissolution even under low pH conditions without undergoing change in solubility even when the pH is increased, thus offering a remarkably improved bioavailability as a whole. The present invention was accomplished based on this finding.

The present invention relates, therefore, to a solid preparation comprising granules each comprises a fine particulate core and a drug layer coated on said fine particulate core, said drug layer comprising (1) an enteric base and (2) a pH-dependent hardly soluble drug which is depressed in solubility with pH elevation and said drug occurring as a solid solution in said enteric base. The object of the invention is to provide such a preparation.

One of the outstanding features of the present invention is as follows. Enteric bases are generally intended to suppress the release of a drug under low pH conditions and allow the drug to be released for the first time under the pH conditions in the intestinal tract. Moreover, it is known in the art that even the solid solution reported in the article in *Yakugaku Zasshi,* referred to above, the solubility is suppressed. However, it was found that the use of a pH-dependent hardly soluble drug, which is depressed in solubility with pH elevation, in combination with a definite amount of an enteric base resulted in a pH-independent quick-dissolution preparation. Accordingly, this pH-dependent hardly soluble drug has a property to be released from an enteric base-containing composition under low pH conditions provided that the drug is combined with a definite amount of the enteric base.

N-(1-Benzyl-2-methylpyrrolidin-3-yl)-5-chloro-2-methoxy-4-methylaminobenzamide, a drug which was found by the inventors to have that unique property, is a compound having the generic name of emonapride and its hydrochloride is called emonapride hydrochloride.

Emonapride and its salt were synthesized for the first time by researchers in the applicant company and are compounds useful as therapeutic agents for schizophrenia and other mental diseases (cf. JP-A-55-16578). The advent of a quick-dissolution preparation has been awaited for use in these indications. Since emonapride and its salt become drastically insoluble under conditions over pH 4, improvement in their solubility has been earnestly demanded.

The quick-dissolution preparation of the present invention is described in detail hereinafter.

The drug to be employed in accordance with this invention is a drug such that its solubility undergoes a sharp decrease with pH elevation but that its pattern of release from a solid preparation containing granules obtained by coating fine particulate cores with a solid solution of the drug and an enteric base is not pH-dependent and efficient, with a consequent marked improvement in bioavailability, thus being not limited to emonapride and its salt. Among drugs of this type may be mentioned nicardipine hydrochloride, amosulalol hydrochloride, noscapine hydrochloride, propafenone hydrochloride, quinine hydrochloride, dipyridamole, josamycin, dilevalol hydrochloride, labetalol hydrochloride and so on.

The drug is incorporated in a sufficient amount that a solid preparation in a unit dosage can provide the expected efficacy and is advantageously incorporated within the range of 0.5 to 10.0% (w/w) or, particularly for providing a small-sized compressed solid preparation, 3.0 to 5.0% (w/w) based on the whole preparation.

The fine particulate core for use in the present invention may be made of any material that may be coated with a solid solution and does not frustrate the object of the invention. Preferred examples of the fine particulate core include calcium hydrogenphosphate, sucrose, lactose, starch and crystalline cellulose.

Two or more of them may be used in combination. The amount of the core material depends on the drug and base used but is preferably within the range of, for example, 5 to 50% (w/w) based on the whole preparation.

The enteric base to be used in the present invention may be any enteric base that is insoluble under low pH conditions or in water and is soluble under high pH conditions, and is more advantageously a pH-dependent enteric base which dissolves under pH conditions over pH 5.

As such enteric bases may be mentioned hydroxypropylmethylcellulose phthalate, methacrylic acid-methyl methacrylate copolymer, cellulose acetate phthalate, hydroxypropylmethylcellulose acetate succinate, carboxymethylethylcellulose, etc., all of which are insoluble in water and dissolve at pH not less than 5.0.

While two or more of these enteric bases may be used in combination, the use of a single species is generally sufficient to achieve the objective effect.

The amount of the enteric base is preferably not more than 5 times, more preferably not more than twice, the amount of the drug used and, based on the whole preparation, is advantageously in the range of 2 to 20% (w/w).

The solid preparation according to the present invention is preferably a tablet but may be any solid preparation that can be administered by the oral route.

The quick-dissolution preparation of the invention can be manufactured by subjecting fine particulate cores to coating and granulation using a solution containing the drug and the enteric base and, after drying, preparing a solid preparation with the addition of an appropriate vehicle, disintegrant, lubricant and/or other additives.

The solvent which dissolves both the drug and enteric base includes, among others, alcohols having a lower boiling point such as methanol, ethanol, etc., ketones such as acetone, methyl ethyl ketone, etc., and organic solvents of halogenated hydrocarbon such as dichloromethane, dichloroethane, etc., inclusive of mixtures of these solvents.

The coating procedure is not limited to fluidized-bed coating method but any technique capable of achieving coating with a solid solution, such as centrifugal coating method, fluidized-bed coating method, etc., can be employed.

The granulation may be carried out simultaneously with coating or immediately after coating, using a coating-granulator-dryer, or by subjecting the coated particles after drying to conventional wet-granulation. The drying process is preferably carried out at a low temperature and sufficient to remove said organic solvent and binder solution, for example at 40° C., for a few hours.

The additives to be incorporated in the quick-dissolution preparation of the present invention, and their respective amounts, are selected according to the type of solid preparation.

The vehicle which can be used includes, among others, starch, lactose, crystalline cellulose, mannitol, sucrose, calcium sulfate, calcium lactate, synthetic aluminum silicate, calcium hydrogenphosphate, silicic anhydride and magnesium aluminometasilicate.

The examples of the disintegrant advantageously used are starch, crystalline cellulose, carboxymethylcellulose calcium, etc. and those of said lubricant are magnesium stearate, talc, hydrogenated vegetable oil, etc., and those of said binder are starch, hydroxypropylcellulose and so on. If necessary, a flavoring agent may be added and even a sugar coat may be applied by the conventional method.

Two or more species of any of these additives can be used in consideration of the objective. The manufacture of tablets can be carried out by whichever of direct compression and wet compression.

The present invention achieved a remarkable effect which is unexpected from the known techniques at all in that an easily absorbable solid preparation excellent in quick and pH-independent dissolution and in bioavailability is provided for a pH-dependent drug which is depressed in solubility with pH elevation.

INDUSTRIAL APPLICABILITY

The following are experiments and results for demonstrating the excellent effects of the solid preparation of the present invention.

EXPERIMENT EXAMPLE 1

Dissolution Test Under Various pH Conditions

| Comparative Example 1 | Emonapride HCl bulk substance |
|---|---|
| Comparative Example 2 | Thirty grams of emonapride | hydrochloride, pulverized in a sample mill, is mixed with 700 g of lactose, 100 g of carboxymethylcellulose calcium, 335.5 g of corn starch and 12 g of calcium stearate and the composition is compression-molded to provide emonapride hydrochloride 3 mg tablets. These 3 mg tablets are designated Tablet A.

Dissolution Test Method

The dissolution test was carried out according to Dissolution Test, Method 2 (paddle method), of Japanese Pharmacopoeia at a paddle speed of 100 rpm. As test solutions, 900 ml of JP Test Solution 1 (pH 1.2) and JP Test Solution 2 (pH 6.8) were used [In the preparation of test solutions, JP Test Solution 1 was used for pH 1.2, acetate buffer (Sørensen buffer) for pH 2.0–5.0, and phosphate buffer (Clark-Lubs buffer) for pH 6.0–7.6, and JP Test Solution 2 for pH 6.8]. The test fluids were continuously filtered through Nucripore Membrane (pore size 0.2 or 0.6 µm).

Separately, about 0.1 g of emonapride hydrochloride was accurately weighed out and dissolved in methanol to make exactly 200 ml. One milliliter portions of this solution were accurately taken out and JP Test Solution 1 and JP Test Solution 2 were added respectively to make exactly 200 ml each for use as standard solutions S1 and S2. For the filtrate and the standard solutions S1 and S2, the absorbance at 313 nm was measured by absorption spectrometry using a Flow cell and the dissolution rate (%) was calculated. The fluid after absorbance measurement was returned to the testing apparatus.

Solubility Determination

Emonapride hydrochloride (0.05–5 g) was added to 10 ml portions of test solutions of various pH and each mixture was shaken at 37° C. for 1 hour, at the end of which it was filtered through Nucripore Membrane (pore size 0.6 µm). A definite portion of the filtrate was taken out and diluted with acetate buffer (pH 3.0) for use as a sample solution.

Separately, about 0.1 g of emonapride hydrochloride was accurately weighed out and dissolved in methanol to make exactly 100 ml. One milliliter portion of this solution was accurately taken out and diluted with acetate buffer (pH 3.0) to make exactly 100 ml for use as the standard solution. For each of the test solution and the standard solution, the absorbance at 313 nm was measured by absorption spectrometry and the solubility was determined.

In the preparation of the test solutions, JP Test Solution 1 was used for pH 1.2, acetate buffer (Sørensen buffer) for pH 2.0–5.0, phosphate buffer (Clark-Lubs buffer) for pH 6.0–7.6 and JP Test Solution 2 for pH 6.8.

(1) Test results are shown in FIG. 1.

It is apparent from these results that while the solubility of emonapride hydrochloride bulc substance was not less than 5000 µg/ml at pH≦4, the solubility decreased sharply as the pH exceeded 4 to become not more than 10 µg/ml at pH≧6.8. Thus, the dissolution is pH-dependent.

(2) The pattern of dissolution of emonapride hydrochloride from Tablet A is shown in FIG. 2.

As a result, as expected, the pattern of dissolution of emonapride hydrochloride from Tablet A decreased sharply as the pH exceeded 4. Thus, the dissolution is highly pH-dependent like that of the bulc substance.

(3) On the other hand, the pattern of dissolution of emonapride hydrochloride from the emonapride hydrochloride 3 mg sugar-coated tablet (hereinafter referred to as Tablet B), which is a tablet containing the solid solution-coated granules as obtained in Example 1, is shown in FIG. 3.

It is apparent from this experimental result that the dissolution of emonapride hydrochloride from Tablet B of the present invention is substantially not influenced by pH and, in addition, the rate of dissolution is high.

(4) On the other hand, the pattern of dissolution of emonapride hydrochloride from the emonapride hydrochloride 10 mg sugar-coated tablet obtained in Example 2 (hereinafter referred to as Tablet C; this tablet is smaller in size than Tablet B) is shown in FIG. 4.

It is seen that although the dissolution pattern is decreased somewhat in the neighborhood of pH 4, the preparation of Example 2, which is reduced in size, showed substantially the same release pattern as Tablet B.

EXPERIMENT EXAMPLE 2

Plasma Concentration of the Unchanged Compound in Dogs

Methods (1) Drug Administration and Blood Sampling

Dogs in groups of 6 individuals were orally dosed with the emonapride HCl 3 mg/kg Tablet A and Tablet B, each together with 20 ml of water. Before administration, the dogs were fasted overnight. The washout period was 6 to 13 days. At 0.5, 1, 2, 4, 6 and 8 hours after administration, the blood was sampled using a heparinized syringe and centrifuged to separate the plasma. The plasma was frozen at –20° C. for preservation till assay.

(2) Determination of the Plasma Concentration of the Unchanged Compound and Calculation of Pharmacokinetic Parameters The unchanged compound in each plasma sample was assayed by the GC/MS (EI-POS) method.

The Cmax is shown in terms of the mean of individual plasma concentration values of the unchanged compound. The AUC was calculated by the trapezoidal method for a period of hours 0 to 8.

Results (1) The mean plasma concentrations of the unchanged compound after oral administration of Tablet A and Tablet B to dogs are shown in FIG. 5.

It is apparent from the above results that Tablet B is a preparation which is scarcely pH-dependent, quick in drug dissolution and having a remarkably improved bioavailability.

BEST MODE OF PRACTICING THE INVENTION

Figure 1:
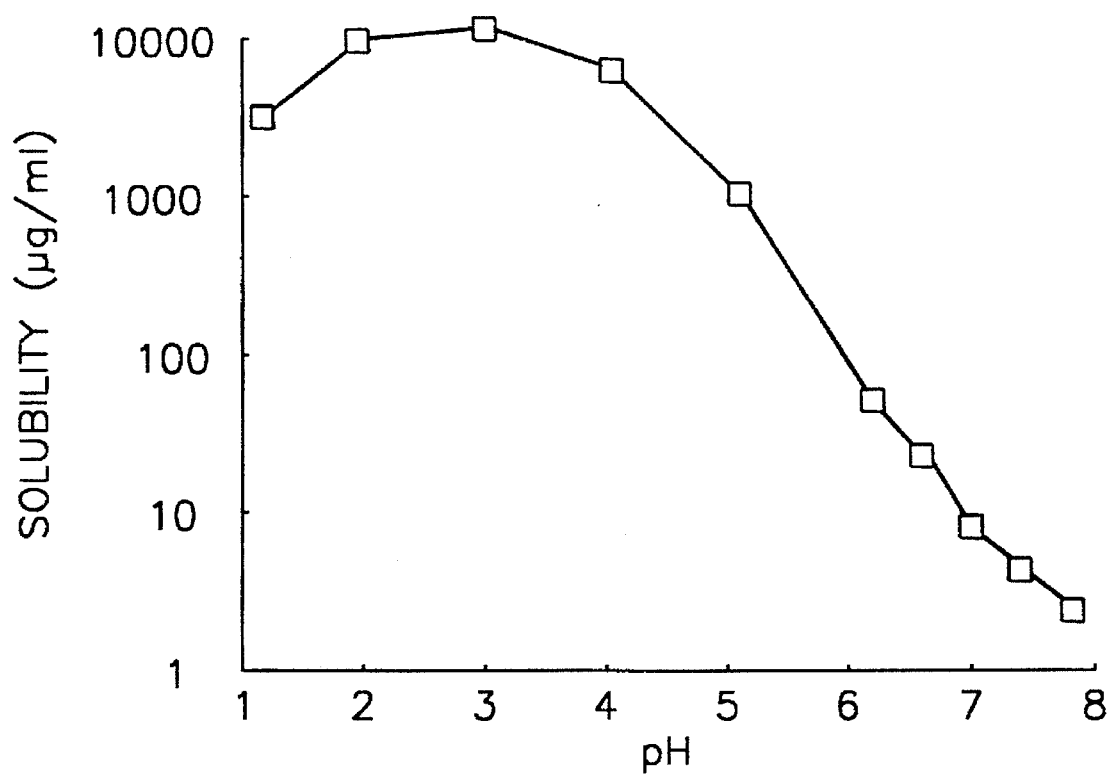
FIG. 1 shows the solubility (37° C.) of emonapride hydrochloride bulc substance in test solutions having various pH.
Figure 2:
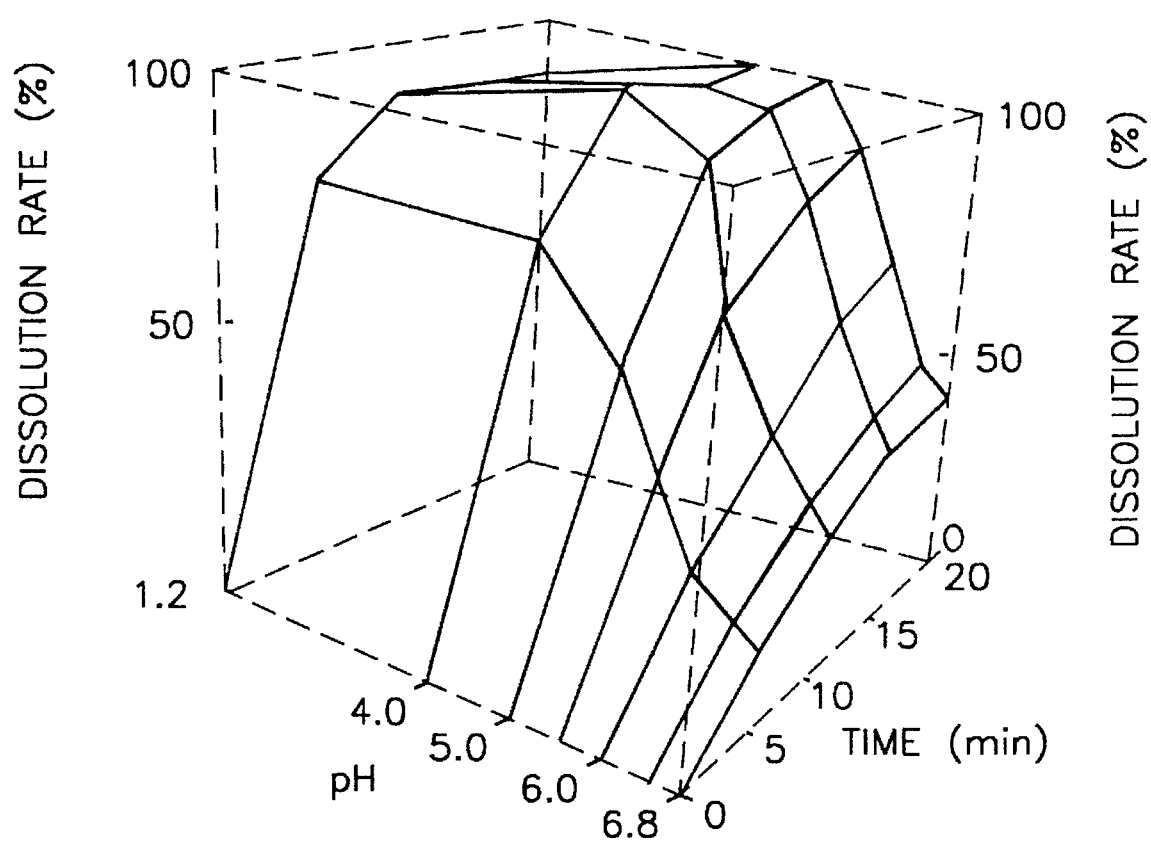
FIG. 2 shows the patterns of dissolution of emonapride hydrochloride from Tablet A, 3 mg, in test solutions having various pH.
Figure 3:
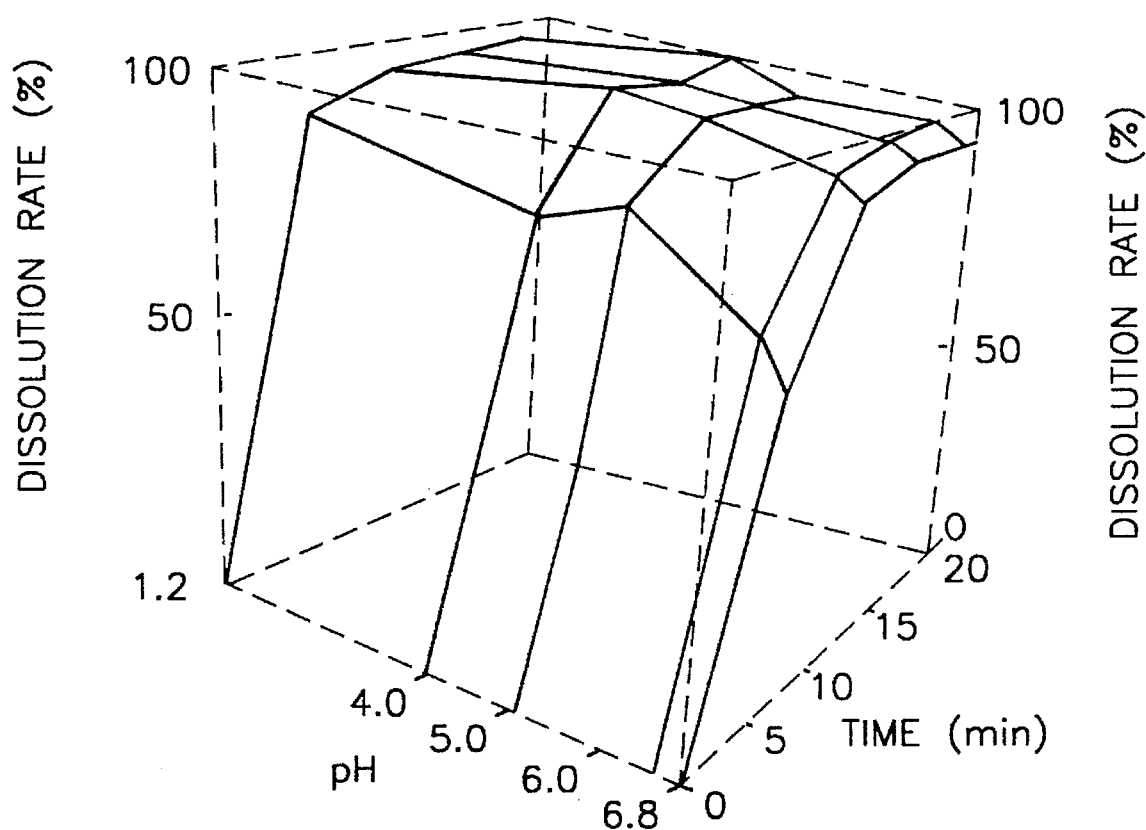
FIG. 3 is the patterns of dissolution of emonapride hydrochloride from Tablet B, 3 mg, in test solutions having various pH.
Figure 4:
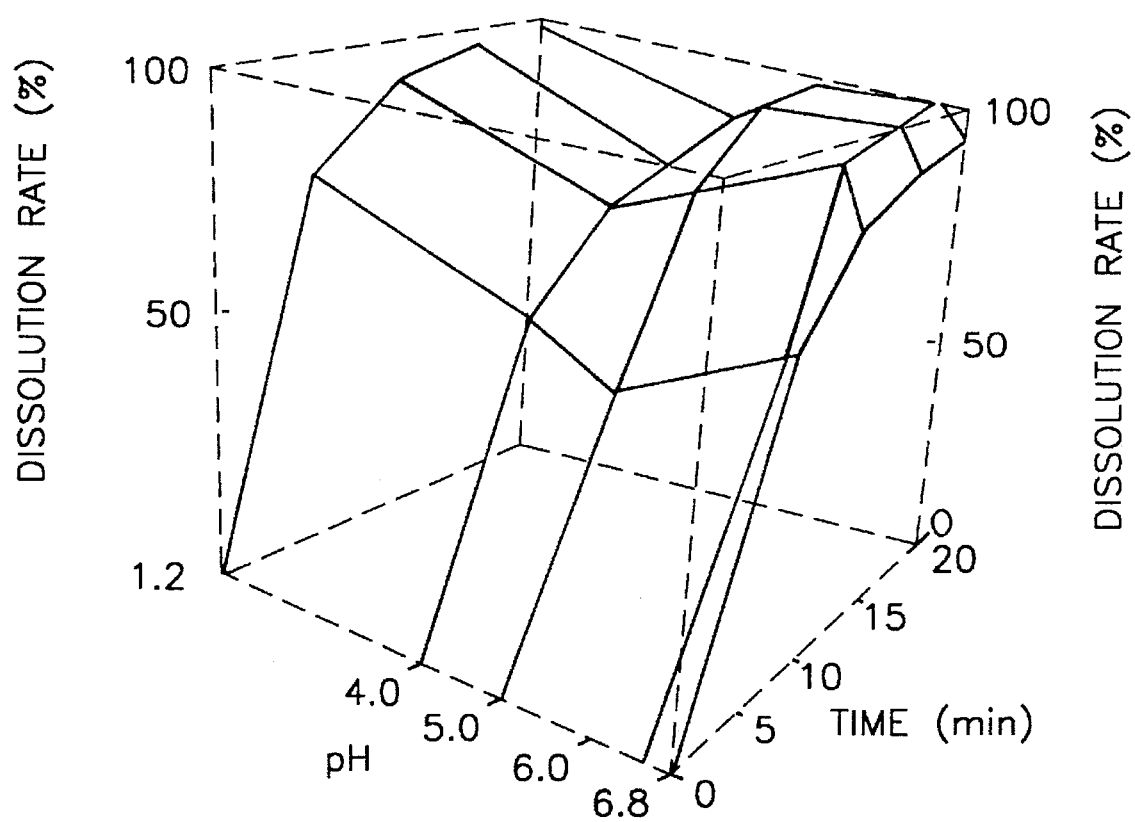
FIG. 4 is the patterns of dissolution of emonapride hydrochloride from Tablet C, 10 mg, in test solutions having various pH.
Figure 5:
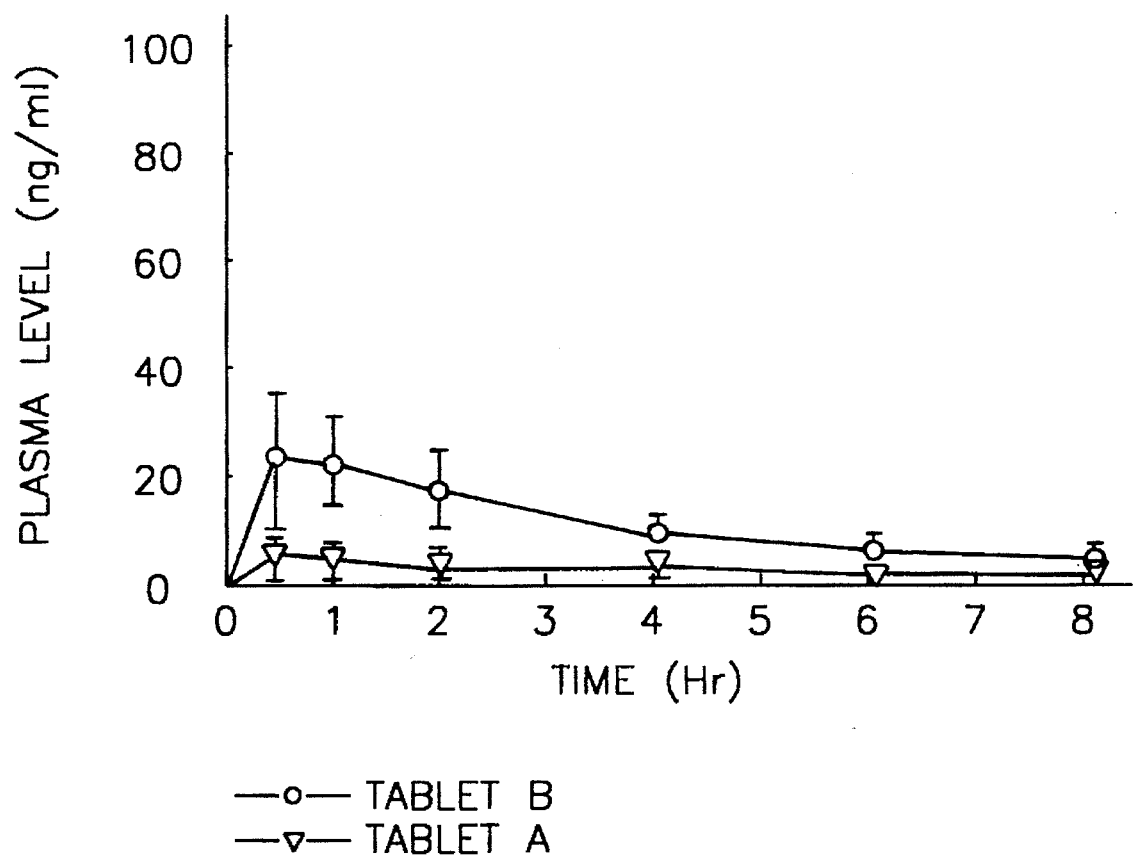
FIG. 5 is the mean plasma concentrations of the unchanged compound after oral administration of the emonapride hydrochloride tablets to dogs.

The following examples are intended to describe the present invention in further detail and should by no means be construed as limiting the scope of the present invention.

EXAMPLE 1 (Tablet B)

In a solvent (methanol 1,140 g, methylene chloride 21,660 g) are dissolved 570 g of emonapride hydrochloride, 1,710 g of hydroxypropylmethylcellulose phthalate 220824 and 570 g of macrogol 400. Then, 570 g of magnesium aluminometasilicate is suspended and using a fluidized-bed granulator (FLO-5), 5,700 g of anhydrous calcium hydrogenphosphate is spray-coated to provide granules. To these granules are added 5,700 g of anhydrous calcium hydrogenphosphate, 5,700 g of crystalline cellulose, 6,840 g of crystalline lactose, 855 g of carboxymethylcellulose calcium and 285 g of calcium stearate and the composition is compression-molded to prepare tablets. The resulting tablets are sugar-coated to provide sugar-coated tablets.

EXAMPLE 2 (Tablet C)

Using a fluidized-bed granulator (FLO-5), a solution containing 600 g of emonapride hydrochloride and 1,200 g of an enteric polymer (hydroxypropylmethylcellulose phthalate 220824) dissolved in a solvent (methanol 680 g, methylene chloride 6,090 g) is sprayed to 3,000 g of anhydrous calcium hydrogenphosphate cores to prepare granules. The granules are mixed with 4,440 g of anhydrous calcium hydrogenphosphate, 2,400 g of crystalline cellulose, 240 g of carboxymethylcellulose calcium and 120 g of calcium stearate and the resulting composition is compression-molded to prepare tablets. The tablets prepared are sugar-coated to provide sugar-coated tablets.

We claim:

1. A pH-independent quick-dissolution solid preparation comprising granules each comprising a fine particulate core and a drug layer coated on said fine particulate core, said drug layer comprising
   (1) an enteric base and
   (2) N-(1-benzyl-2-methylpyrrolidin-3-yl)-5-chloro-2-methoxy-4-methylaminobenzamide, or a salt thereof, being a pH-dependent hardly soluble drug which is depressed in solubility with pH elevation and said drug occurring as a solid solution in said enteric base, wherein the amount of said pH-dependent hardly soluble drug solution is 0.5% to 10% (w/w) based on the total amount of the preparation, and the amount of said enteric base is not more than 5 times the amount of said pH-dependent hardly soluble drug and is 2 to 20% (w/w) based on the total amount of the preparation.

2. The quick-dissolution solid preparation according to claim 1 wherein said enteric base is hydroxypropylmethylcellulose phthalate.

3. The quick-dissolution solid preparation according to claim 1 wherein the amount of said enteric base is not more than 2 times the amount of said pH-dependent hardly soluble drug.

4. The quick-dissolution solid preparation according to claim 1 wherein said enteric base has the ability to dissolve at pH not lower than 5.

* * * * *